United States Patent
You et al.

(10) Patent No.: US 12,013,393 B2
(45) Date of Patent: *Jun. 18, 2024

(54) RAMAN-ACTIVE NANOPARTICLES AND METHOD OF PREPARING THE SAME

(71) Applicant: KOREA RESEARCH INSTITUTE OF STANDARDS AND SCIENCE, Daejeon (KR)

(72) Inventors: Eun-Ah You, Daejeon (KR); Wansun Kim, Daejeon (KR); Tae Geol Lee, Daejeon (KR)

(73) Assignee: KOREA RESEARCH INSTITUTE OF STANDARDS AND SCIENCE, Daejeon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/498,326

(22) PCT Filed: Oct. 10, 2018

(86) PCT No.: PCT/KR2018/011873
§ 371 (c)(1),
(2) Date: Sep. 26, 2019

(87) PCT Pub. No.: WO2020/075879
PCT Pub. Date: Apr. 16, 2020

(65) Prior Publication Data
US 2021/0364509 A1 Nov. 25, 2021

(30) Foreign Application Priority Data
Oct. 8, 2018 (KR) ........................ 10-2018-0119894

(51) Int. Cl.
*G01N 33/553* (2006.01)
*B82Y 30/00* (2011.01)
(Continued)

(52) U.S. Cl.
CPC ..... *G01N 33/54346* (2013.01); *G01N 33/553* (2013.01); *B82B 1/008* (2013.01);
(Continued)

(58) Field of Classification Search
CPC ........... G01N 33/54346; G01N 33/553; G01N 21/658; B82B 1/008; B82Y 5/00; B82Y 15/00; B82Y 40/00; B82Y 30/00
See application file for complete search history.

(56) References Cited

U.S. PATENT DOCUMENTS

2013/0115254 A1* 5/2013 Odom ................ A61K 41/0042
977/773
2015/0018807 A1* 1/2015 Kircher .................. A61B 18/02
606/12

(Continued)

FOREIGN PATENT DOCUMENTS

JP 2012-008144 A 1/2012
KR 10-2012-0132668 A 12/2012
(Continued)

OTHER PUBLICATIONS

Tian et al. ("Highly sensitive detection of exosomes by SERS using gold nanostar@Raman reporter@nanoshell structures modified with a bivalent cholesterollabeled DNA anchor," Analyst, 2018, vol. 143, pp. 4915-4922, published on Sep. 10, 2018) (Year: 2018).*

(Continued)

*Primary Examiner* — Shafiqul Haq
*Assistant Examiner* — Nam P Nguyen
(74) *Attorney, Agent, or Firm* — Knobbe, Martens, Olson & Bear, LLP

(57) ABSTRACT

Provided is a method of preparing Raman-active nanoparticles, which includes a) preparing a metal nanocore having a nano-star shape from a first reaction solution in which a first metal precursor is mixed with a buffer solution; b) fixing (Continued)

a Raman reporter in the metal nanocore; and c) forming a metal shell, which surrounds the nanocore in which the Raman reporter is fixed, from a second reaction solution in which a second metal precursor is mixed with the nanocore in which the Raman reporter is fixed. The Raman reporter has a binding affinity for each of a first metal of the metal nanocore and a second metal of the metal shell.

5 Claims, 3 Drawing Sheets

(51) Int. Cl.
*G01N 33/543* (2006.01)
*B82B 1/00* (2006.01)
*B82Y 5/00* (2011.01)
*B82Y 15/00* (2011.01)
*B82Y 40/00* (2011.01)
*G01N 21/65* (2006.01)

(52) U.S. Cl.
CPC ............. *B82Y 5/00* (2013.01); *B82Y 15/00* (2013.01); *B82Y 40/00* (2013.01); *G01N 21/658* (2013.01)

(56) References Cited

U.S. PATENT DOCUMENTS

2021/0331933 A1* 10/2021 You .................. G01N 21/658
2023/0103705 A1* 4/2023 You .................. G01N 33/483
356/301

FOREIGN PATENT DOCUMENTS

| KR | 10-2014-0101980 A | 8/2014 |
|---|---|---|
| KR | 10-1486697 B1 | 1/2015 |
| KR | 10-2017-0129633 A | 11/2017 |
| KR | 10-2020-0040111 A | 4/2020 |

OTHER PUBLICATIONS

Hampton Research (https://hamptonresearch.com/product-Sodium-citrate-tribasic-dihydrate-Buffer-135.html, retrieved on May 20, 2022). (Year: 2022).*
Tian Il et al., "Gold nanostars for efficient in vitro and in vivo real-time SERS detection and drug delivery via plasmonic-tunable Raman/FTIR imaging", Biomaterials, vol. 106, pp. 87-97, published 2016. (Year: 2016).*
Xie et al., "Seedless, Surfactantless, High-Yield Synthesis of Branched Gold Nanocrystals in HEPES Buffer Solution", Chem. Mater., vol. 19, pp. 2823-2830, published May 8, 2007. (Year: 2007).*
Office Action of corresponding Korean Patent Application No. 10-2018-0119894—3 pages (Feb. 14, 2020).
Xu et al., "Preparation of Au—Ag coreshell nanoparticles and application of bimetallic sandwich in surface-enhanced Raman scattering (SERS)", Colloids and Surfaces A: Physicochem. Eng. Aspects—6 pages (2005).
Zhang et al., "Gold and silver nanoparticle monomers are non-SERS-active: a negative experimental study with silica-encapsulated Raman-reporter-coated metal colloids", Phys. Chem. Chem. Phys., Issue 17—9 pages (2015).
Khlebtsov et al., "A New Typle of SERS Tags: Au@Ag Core/Shell Nanorods with Embedded Aromatic Molecules", Nanotechnologies in Russia, vol. 12, Nos. 9-10—14 pages (2017).
International Search Report of corresponding PCT Application No. PCT/KR2018/011873—4 pages (Jul. 5, 2019).
Written Opinion of the International Search Authority of corresponding PCT Application No. PCT/KR2018/011873—4 pages (Jul. 5, 2019).
Notice of Allowance of corresponding Korean Patent Application No. 10-2018-0119894—5 pages (May 9, 2020).

* cited by examiner

[Figure 1]
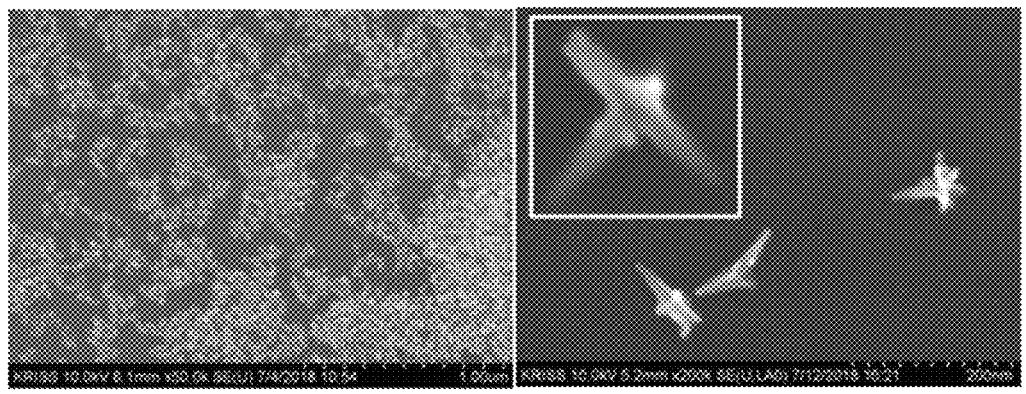
[Figure 2]
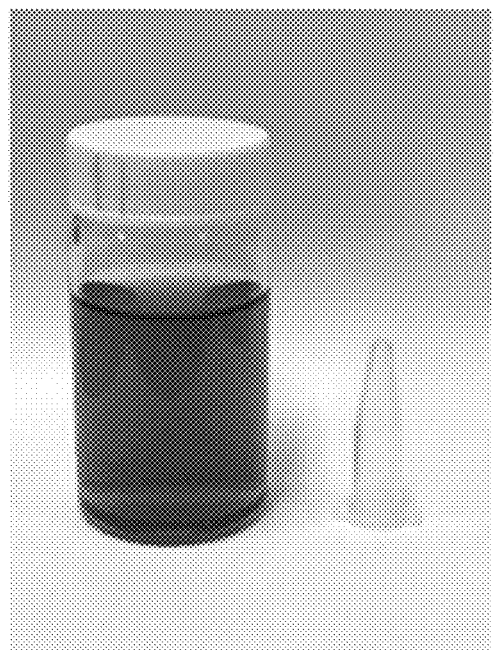

[Figure 3]
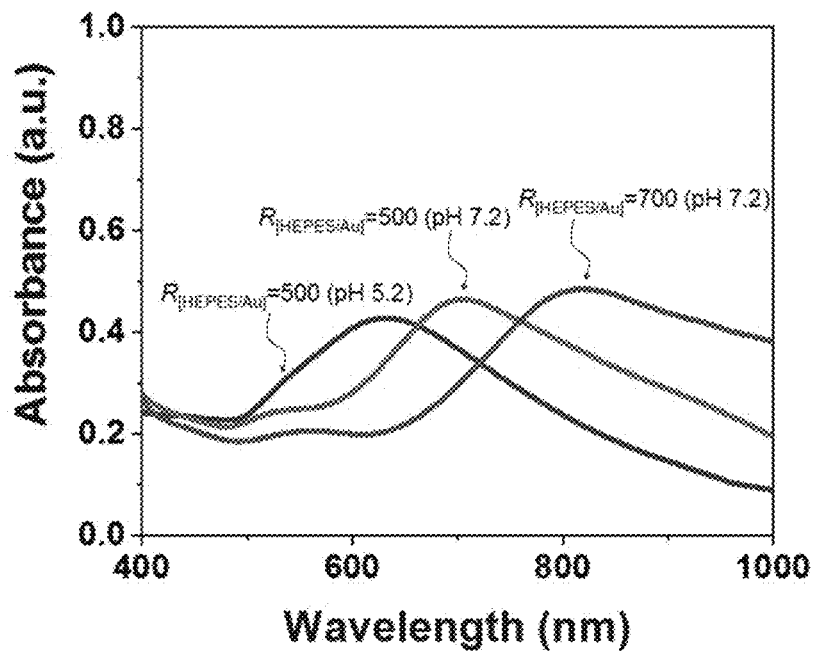
[Figure 4]
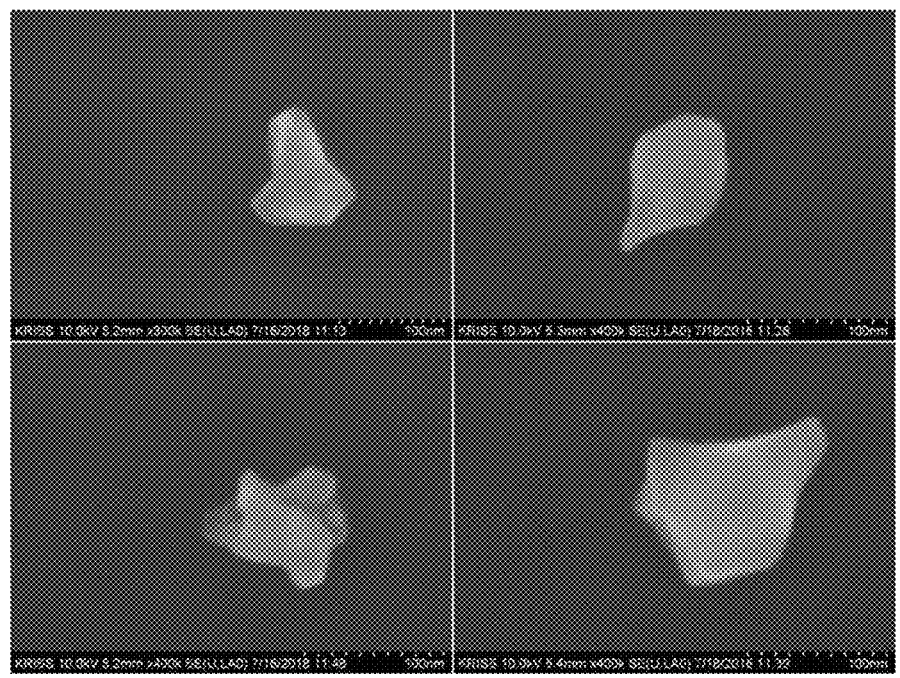

[Figure 5]
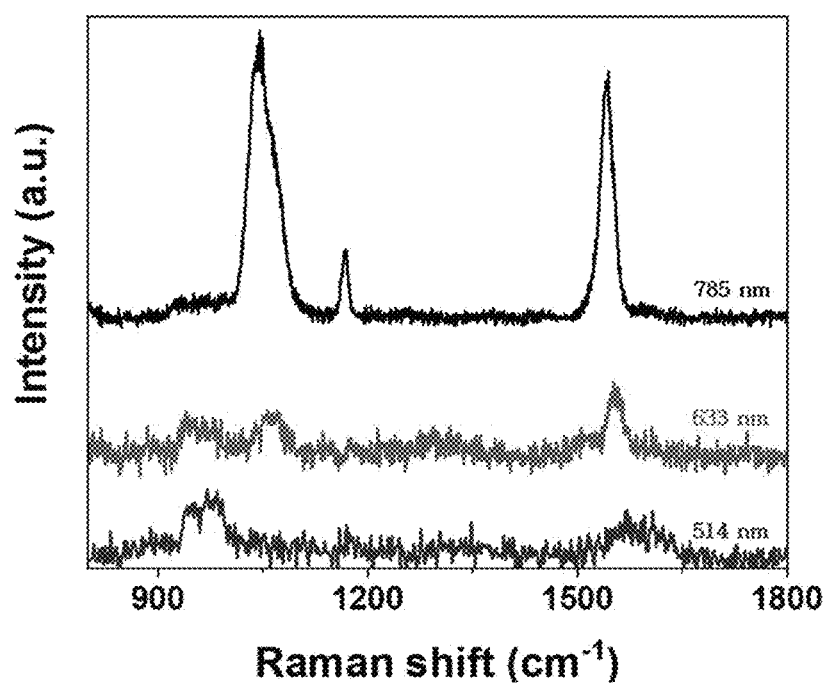

RAMAN-ACTIVE NANOPARTICLES AND METHOD OF PREPARING THE SAME

CROSS-REFERENCE TO RELATED APPLICATIONS

This application claims priority under 35 U.S.C. § 119 to Korean Patent Application No. 10-2018-0119894, filed on Oct. 8, 2018, in the Korean Intellectual Property Office, the disclosure of which is incorporated herein by reference in its entirety.

TECHNICAL FIELD

Technical Field

The present invention relates to Raman-active nanoparticles and a method of preparing the same, and more particularly, to nanoparticles having a surface-enhanced Raman scattering (SERS) activity and a method of preparing the same.

Background Art

Surface-enhanced Raman scattering (hereinafter referred to as "SERS") spectrometry uses a phenomenon in which the intensity of Raman scattering greatly increases $10^6$ to $10^8$-fold or more when molecules are adsorbed onto a nanostructure surface of a metal such as gold, silver, and the like. This is high-sensitivity technology that may be combined with the nanotechnology, which has currently developed very rapidly, to directly measure only one molecule, and particularly has been highly anticipated as being imperatively used as a medical sensor.

SERS spectrometry is a measuring technique having high selectivity and high informativity, and also is a potent analysis method for supersensitive chemical/biological/biochemical analysis. Thus, much research is being conducted to make early diagnosis of various diseases including Alzheimer's disease, diabetes, and the like, as well as high-sensitivity DNA analysis.

For detection of SERS spectroscopy-based materials, it is typical to make use of a hot spot (KR2017-0129633) formed in a position in which a plasmon metal in the form of particles or wires is positioned on a plasmon metal thin film or to make use of a SERS substrate based on a hot spot formed by contact between two or more plasmon particles.

However, the hot spot formed by contact between such two constituent elements has a problem in that it is difficult to detect biochemical materials (e.g., biomaterials) having a size of several or several tens of micrometers because the surface-enhanced Raman scattering has a limited size and occurs only in a very limited area (referred to as a nanogap) between the two constituent elements.

Also, the biochemical materials or bio-derived materials have a drawback in that it is difficult to obtain a pure Raman spectrum because a fluorescence phenomenon occurs when these materials are irradiated with visible rays.

Accordingly, there is a need for development of Raman-active and plasmon-active particles capable of making SERS analysis through irradiation with light having a band of near-infrared rays rather than the visible rays and enhancing signals without any limitation on the size of an analyte.

DISCLOSURE

Technical Problem

An aspect of the present invention is to provide Raman-active nanoparticles having a Raman activity, specifically a surface-enhanced Raman scattering activity (hereinafter referred to as "SERS activity") being free from the limitation on the size of an analyte, and a method of preparing the same.

Another aspect of the present invention is to provide Raman-active nanoparticles in which an organic matter including a Raman reporter is stably protected from external environments, and a method of preparing the same.

Still another aspect of the present invention is to provide Raman-active nanoparticles capable of generating remarkably improved Raman scattering signals because two different hot spots are positioned on the particles themselves, and a method of preparing the same.

Yet another aspect of the present invention is to provide Raman-active nanoparticles capable of tuning a localized surface plasmon resonance (LSPR) wavelength to a wide extent, and a method of preparing the same.

Yet another aspect of the present invention is to provide a preparation method capable of mass-producing the Raman-active nanoparticles having excellent durability and high SERS activity in a short period of time.

Technical Solution

In one general aspect, a method of preparing Raman-active nanoparticles according to the present invention includes: a) preparing a metal nanocore having a nano-star shape from a first reaction solution in which a first metal precursor is mixed with a buffer solution; b) fixing a Raman reporter in the metal nanocore; and c) forming a metal shell, which surrounds the nanocore in which the Raman reporter is fixed, from a second reaction solution in which a second metal precursor is mixed with the nanocore in which the Raman reporter is fixed, wherein the Raman reporter has a binding affinity for each of a first metal of the metal nanocore and a second metal of the metal shell.

In the method of preparing Raman-active nanoparticles according to one embodiment of the present invention, a self-assembled monolayer of the Raman reporter surrounding the metal nanocore may be formed in the step b).

In the method of preparing Raman-active nanoparticles according to one embodiment of the present invention, a shape, a size, or both the shape and the size of the nanocore may be adjusted by controlling one or more factors selected from a molar ratio of the first metal precursor to a buffer agent of the buffer solution; and a pH of the buffer solution.

In the method of preparing Raman-active nanoparticles according to one embodiment of the present invention, a molar ratio R1 obtained by dividing the number of moles of the buffer agent by the number of moles of the first metal precursor may be in a range of 200 to 750.

In the method of preparing Raman-active nanoparticles according to one embodiment of the present invention, the second reaction solution may include a surfactant, or may include a surfactant and an organic acid.

In the method of preparing Raman-active nanoparticles according to one embodiment of the present invention, the buffer solution may contain one or more selected from 4-(2-hydroxyethyl)-1-piperazineethanesulfonic acid (HEPES), 4-(2-hydroxyethyl)piperazine-1-ethanesulfonic acid (MES), phosphated buffered saline (PBS), tris(2-amino-2-hydroxymethyl propne-1,3-idol), phosphate buffer (PB), 3-(N-morpholino)propanesulfonic acid (MOPS), 3-[[1,3-dihydroxy-2-(hydroxymethyl)propan-2-yl]amino] propane-1-sulfonic acid (TAPS), and piperazine-N,N'-bis(2-ethanesulfonic acid) (PIPES).

In the method of preparing Raman-active nanoparticles according to one embodiment of the present invention, a metal of the metal precursor may be Au or Ag.

After the step c), the method of preparing Raman-active nanoparticles according to one embodiment of the present invention may further include: d) fixing a receptor, which binds to an analyte, in the metal shell.

In another general aspect, there are provided Raman-active nanoparticles prepared by the method of preparing Raman-active nanoparticles as described above.

In still another general aspect, Raman-active nanoparticles according to the present invention include: a metal nanocore having a nano-star shape; self-assembled monolayer including a Raman reporter fixed in the metal nanocore; and a metal shell surrounding the self-assembled monolayer, wherein the Raman-active nanoparticles have a protruding structure due to the nano-star shape of protrusions.

In the Raman-active nanoparticles according to one embodiment of the present invention, the Raman-active nanoparticles may have a shape corresponding to the nano-star shape of the metal nanocore.

In the Raman-active nanoparticles according to one embodiment of the present invention, the metal nanocore may include a central region having a size of 10 to 50 nm and protrusions having a size of 5 to 70 nm and protruding from the central region to taper in a protruding direction.

In the Raman-active nanoparticles according to one embodiment of the present invention, the Raman-active nanoparticles may further include a receptor fixed in the metal shell to bind to an analyte.

Advantageous Effects

The Raman-active nanoparticles according to the present invention have an advantage in that, because the hot spots are positioned in the nanoparticles themselves, the analyte can be analyzed when the analyte is simply bound to the nanoparticles, and there is no limitation on the size of the analyte.

Also, the Raman-active nanoparticles according to the present invention have an advantage in that the analyte can be analyzed by means of irradiation with near-infrared rays because the nanoparticles have a very wide tuning range of LSPR wavelengths (including a region of 800 nm).

In addition, the Raman-active nanoparticles according to the present invention have advantages in that, because the nanoparticles include the metal nanocore having a nano-star shape, the strong hot spots may be positioned in the nanoparticles themselves, and the nanogap (hot spot) having a uniform size can be formed between the metal nanocore and the metal shell over the entire region of the Raman-active nanoparticles, and the very high enhancement of the Raman signals can be realized when the Raman reporter is positioned in the nanogap (i.e., hot spot).

Additionally, the Raman-active nanoparticles according to the present invention have an advantage in that the nanoparticles have very excellent durability and physical/chemical stability because the organic component including the Raman reporter is surrounded by the metal shell so that the organic component is protected by the metal shell, and the self-assembled monolayer of the Raman reporter and the metal shell are strongly bound to each other via the two functional groups of the Raman reporter.

Further, the method of preparing Raman-active nanoparticles according to the present invention has an advantage in that the Raman-active nanoparticles having the aforementioned advantages can be mass-produced at room temperature in a short period of time using highly simple methods.

DESCRIPTION OF DRAWINGS

FIG. 1 is a scanning electron microscope image for observing a metal nanocore prepared according to one embodiment of the present invention.

FIG. 2 is an optical image for observing a Au nanocore dispersion dispersed in a HEPES buffer solution.

FIG. 3 is a graph for measuring the optical absorbance of a metal nanocore prepared according to one embodiment of the present invention.

FIG. 4 is a scanning electron microscope image for observing Raman-active nanoparticles prepared according to one embodiment of the present invention.

FIG. 5 is a graph showing the surface-enhanced Raman scattering (SERS) spectrum of the Raman-active nanoparticles prepared according to one embodiment of the present invention.

BEST MODE

Hereinafter, Raman-active nanoparticles according to the present invention and a method of preparing the same will be described in detail with reference to the accompanying drawings. The drawings presented hereinbelow are shown as one example to sufficiently provide the scope of the present invention to those skilled in the art. Therefore, it should be understood that the present invention may be embodied in various forms, but is not intended to be limiting in the drawings presented hereinbelow. In this case, the drawings presented hereinbelow may be shown in an exaggerated manner to make the scope of the present invention more clearly apparent. In this case, unless otherwise defined, the technical and scientific terms used herein have the same meaning as commonly understood by one of ordinary skill in the art to which the present invention pertains. In the following description and the accompanying drawings, a description of known functions and configurations, which may unnecessarily obscure the subject matter of the present invention, will be omitted. Unless otherwise particularly defined, in the following context, the unit "solution" refers to an aqueous solution including deionized water, and the unit "concentration" refers to a molar concentration.

A method of preparing Raman-active nanoparticles according to the present invention includes: a) preparing a metal nanocore having a nano-star shape from a first reaction solution in which a first metal precursor is mixed with a buffer solution; b) fixing a Raman reporter in the metal nanocore; and c) forming a metal shell, which surrounds the nanocore in which the Raman reporter is fixed, from a second reaction solution in which a second metal precursor is mixed with the nanocore in which the Raman reporter is fixed, wherein the Raman reporter has a binding affinity for each a first metal of the metal nanocore and a second metal of the metal shell.

In this case, the nano-star shape may be a shape including a single central region and one or more protrusions, particularly two or more, more particularly 2 to 10, and further particularly 3 to 8 protrusions which protrude from the central region to taper in a protruding direction. The specific shape of the protrusions may be a polypyramidal or conical shape, and the like, but the present invention is not particularly limited thereto. When the metal nanocore has two or more protrusions, the shapes or sizes (protruding lengths) of the respective protrusions may be the same as or different from each other. When the metal nanocore has two or more protrusions, the two or more protrusions may have a symmetric relation with respect to the central region, may have a constant angle formed with each other, or may have protrusions protruding from the central region in random positions.

In the method of preparing Raman-active nanoparticles according to the present invention as described above, because the metal nanocore is prepared from a solution containing a buffer solution and a metal precursor, a surface of the metal nanocore is not in a state in which an organic matter (for example, a surfactant, and the like) is strongly bound to the metal nanocore, but may be in a bare metal state. Therefore, the Raman reporter may be stably fixed in an entire region of the metal nanocore in the form of a self-assembled monolayer when the Raman reporter is fixed in the step b).

Therefore, in the method of preparing Raman-active nanoparticles according to one embodiment of the present invention, the first reaction solution may not contain a surfactant (an organic surfactant). In addition, the first reaction solution may not contain both a surfactant and an organic acid.

Also, the method of preparing Raman-active nanoparticles according to the present invention has an advantage in that the Raman-active nanoparticles may be mass-produced at low cost in a short period of time because the Raman-active nanoparticles are prepared using a simple process, which includes forming a metal nanocore using a solution containing a buffer solution and a metal precursor, attaching a Raman reporter, and forming a metal shell.

In addition, the method of preparing Raman-active nanoparticles according to the present invention has an advantage in that an organic matter including the Raman reporter may be stably protected from external environments because the organic matter including the Raman reporter is not exposed to surfaces of the Raman-active nanoparticles, and is surrounded by the metal shell.

Furthermore, the method of preparing Raman-active nanoparticles according to the present invention has an advantage in that the Raman-active nanoparticles themselves can enhance scattering signals because a hot spot is formed in the metal nanocore itself when the metal nanocore has a nano-star shape.

In this case, as known in the art, the hot spot refers to a region in which a very strong local electric field is formed and localized surface plasmon resonance (LSPR) is generated.

When the signals are enhanced by hot spots between two separate constituent elements, such as between nanoparticles, between the nanoparticles and other constituent elements, or the like, the signals may be enhanced even when an analyte is positioned in (or bound to) a nanogap region between two constituent elements or a region around the nanogap. Such a spatial constraint limits the size of the analyte, thereby making it impossible to analyze a biochemical material having a size of several or several tens of micrometers.

However, when a single Raman-active nanoparticle in an individually separated state itself has a hot spot, the signals may be enhanced just when the analyte is bound to the Raman-active nanoparticles. Therefore, the single Raman-active nanoparticle is generally very suitable for detection/analysis of the biochemical material having a large size (the order of several hundreds of nanometers to the order of several tens of micrometers) because there is no substantial limitation on the size of the analyte.

Also, the method of preparing Raman-active nanoparticles according to the present invention has an advantage in that, when the metal nanocore has a nano-star shape, the LSPR wavelength may be tuned to a very wide extent by adjusting a spherical shape or size (including the length of a protruding branch, or the like) of a nano-star.

As one specific example, when the metal nanocore has a nano-star shape, the LSPR wavelength may also be tuned to a wavelength range of 800 nm at which the LSPR wavelength may not be tuned in a spherical shape. By the LSPR wavelength which may be tuned to this wavelength range of 800 nm or more, it may be meant that detection and analysis of the analyte may be achieved through irradiation with light having a band of near-infrared rays (NIR, 780 nm to 1,500 nm) rather than a band of visible rays.

When a biomaterial including the biochemical material is irradiated with visible rays, as known in the art, a fluorescence phenomenon may occur. Because the intensity of fluorescence is much stronger than that of Raman scattering, and the fluorescence occurs in a region similar to that of Raman scattering, the Raman spectrum may overlap with fluorescence peaks, which makes it difficult to obtain the pure Raman spectrum. Therefore, the SERS analysis through irradiation with light having a band of near-infrared rays rather than visible rays is very favorable in the field of biology because the Raman spectrum may be obtained without any effect (interference) of fluorescence.

The shape, the size, or both the shape and the size of the metal nanocore may be adjusted by controlling one or more factors selected from the molar ratio of the first metal precursor to a buffer agent of the buffer solution, and the pH of the buffer solution. In this case, it is reasonable that the buffer solution may contain a conventional inorganic acid such as HCl, or the like, a conventional inorganic base such as NaOH, or the like, and a mixture thereof in order to regulate the PH.

As one specific example, the molar ratio R1 obtained by dividing the number of moles of the buffer agent in the first reaction solution by the number of moles of the first metal precursor may be in a range of 200 to 750. The metal nanocore having a nano-star shape may be prepared in this R1 range. That is, the metal nanocore having a nano-star shape, which has a central region having a size of 10 to 50 nm, particularly a size of 10 to 40 nm, may be prepared.

Favorably, R1 may be in a range of 500 to 750. When R1 is controlled to 500 to 750, the metal nanocore having a nano-star shape, which includes 3 or more protrusions, particularly 3 to 8 protrusions, may be prepared, wherein the protrusions have a size of 5 to 70 nm, particularly 5 to 50 nm, and more particularly 10 to 50 nm.

Also, when the R1 is controlled in a range of 200 to 750, the lengths of the protrusions (i.e., extrusions or branches) protruding from the central region of the metal nanocore may be adjusted. As one more specific example, an R1 value may increase in a range of 200 to 750 to increase the lengths of the protrusions. In this case, the LSPR wavelength of the Raman-active nanoparticles (or metal nanocore) may be adjusted by adjusting the lengths of the protrusions. In this case, the LSPR wavelength may be adjusted to 600 to 900 nm by adjusting the R1 in a range of 200 to 750.

The lengths of the protrusions protruding from the central region of the metal nanocore may be adjusted by regulating the pH of the buffer solution, in connection with R1 or independently from of R1 (at constant R1). Specifically, the pH of the buffer solution may be in a range of 5.0 to 7.5, and the lengths of the protrusions may increase by raising the pH of the buffer solution.

The buffer solution (or a buffer agent) may contain one or more selected from 4-(2-hydroxyethyl)-1-piperazineethanesulfonic acid (HEPES), 4-(2-hydroxyethyl)piperazine-1-ethanesulfonic acid (MES), phosphated buffered saline (PBS), tris(2-amino-2-hydroxymethyl propne-1,3-idol), phosphate buffer (PB), 3-(N-morpholino)propanesulfonic acid (MOPS), 3-[[1,3-dihydroxy-2-(hydroxymethyl)propan-2-yl]amino]propane-1-sulfonic acid (TAPS), and piperazine-N,N'-bis(2-ethanesulfonic acid) (PIPES). Because such a buffer agent may serve as a weak reducing agent for reducing a metal, and may exclude a surfactant for promoting stabilization of the metal nanocore by the buffer agent, the metal nanocore having a bare metal surface may be prepared. In this case, as described above, it is reasonable that the buffer solution (i.e., an aqueous solution) may further contain an inorganic acid and/or an inorganic base to regulate the pH.

The first metal of the first metal precursor may be a metal that generates surface plasmons by means of interaction with light. As a specific example, the first metal may include gold, silver, platinum, palladium, nickel, aluminum, copper, or a mixture or an alloy thereof. However, the first metal may be gold or silver in consideration of the stability with respect to the bio-derived material or the biochemical material. In the first metal according to one favorable example, the first metal precursor may be a gold precursor such as $HAuCl_4$, $HAuBr_4$, $NaAuCl_4$, $AuCl_3 \cdot 3H_2O$, $NaAuCl_4 \cdot 2H_2O$, or a mixture thereof, or may be a silver precursor such as $AgNO_3$, or the like. However, it is reasonable that the present invention is not limited to the types of spherical materials of the metal precursor.

More particularly, the step a) may include mixing a first metal precursor solution with a buffer solution to prepare a first reaction solution, and reacting the first reaction solution at a temperature of 15 to 40° C. to prepare the metal nanocore.

A molar concentration of the buffer agent in the buffer solution may be in a range of 100 to 400 mM, and a molar concentration of the first metal precursor in the first metal precursor solution may be in a range of 20 to mM. When the buffer solution and the first metal precursor solution having such molar concentrations are used, it is favorable that most of the first metal precursor added may be converted into the metal nanocore, and the reaction (synthesis of the metal nanocore) may be completed in a reaction time of 10 to 50 minutes. However, the concentration of the buffer solution and the concentration of the first metal precursor solution are not particularly limited to these concentration ranges as described above. When the first metal precursor solution is mixed with the buffer solution, it is reasonable that the solutions may be mixed to satisfy the aforementioned R1.

The reaction may occur while mixing the first metal precursor solution with the buffer solution. In this case, the reaction may be performed at a temperature of 15 to ° C., particularly a temperature of 15 to 35° C., more particularly a temperature of 15 to 25° C., and further particularly room temperature (21 to 23° C.). In this case, it is reasonable that the room temperature may refer to a temperature in a state in which heat energy is not artificially applied to the first reaction solution. The reaction time may be suitable as long as it is a sufficient time to complete the synthesis of the metal nanocore. As a specific example, the reaction time may be in a range of 10 to 50 minutes, and more specifically 20 to 40 minutes, but the present invention is not limited thereto.

If at all, the first reaction solution may be optionally stirred during the reaction of the first reaction solution. When the reaction solution is stirred, the reaction yield may be improved, but the shape or the size of the prepared metal nanocore may be slightly affected by the stirring conditions. The stirring is sufficient as long as the stirring rate is in a range of approximately 500 rpm to 1,500 rpm.

Also, the step a) may include: a1) mixing the first metal precursor solution with the buffer solution to prepare a first reaction solution and reacting the first reaction solution at a temperature of 15 to 40° C. to prepare a metal nanocore; and a2) storing the first reaction solution whose reaction has been completed as a dispersion medium or stock solution for the metal nanocore at a temperature of 1 to 10° C., and particularly a temperature of 1 to 5° C. That is, after the reaction of a1) is completed, the metal nanocore may be stored in a state of the first reaction solution containing the metal nanocore without being separated and recovered from the first reaction solution whose reaction has been completed. In this case, the metal nanocore may be stored at a low temperature of 1 to 10° C., and particularly a low temperature of 1 to 5° C. On the other hand, the step a) may optionally include: a1) mixing the first metal precursor solution with the buffer solution to prepare a first reaction solution and reacting the first reaction solution at a temperature of 15 to 40° C. to prepare a metal nanocore; and a2) recovering the metal nanocore from the first reaction solution whose reaction has been completed and dispersing the metal nanocore in a buffer solution (a separate buffer solution) to store the metal nanocore dispersion at a temperature of 1 to 10° C., and particularly a temperature of 1 to 5° C.

When the metal nanocore prepared in the step a1) is stored at a low temperature of 1 to 10° C. using the reaction solution or buffer solution whose reaction has been completed as the dispersion medium other than the dispersion medium including water, plasmonic-active characteristics of the metal nanocore may be stably retained without any change in the plasmonic-active characteristics even when the metal nanocore is stored for several tens of days.

In this case, as described above, the first reaction solution may not contain a surfactant, which may serve as a reducing agent and simultaneously improve stabilization and dispersing properties of the nanoparticles as well, an organic acid, or both the surfactant and the organic acid. In this case, the step a1) may be performed using only the buffer solution and the first metal precursor solution. As such, the preparation method according to the present invention is very suitable for mass production of the metal nanocore because the two solutions may be simply mixed and the metal nanocore may be synthesized at room temperature in several tens of minutes.

After the step a) is performed, fixing a Raman reporter in the metal nanocore (step b)) may be performed.

The Raman reporter may refer to an organic compound (i.e., an organic molecule) that includes a Raman-active molecule, and may refer to an organic compound (i.e., an organic molecule) that has a binding affinity for a metal of the metal nanocore and includes a Raman-active molecule. Any of the Raman reporters may be used without limitation as long as the Raman reporters are already known and widely used in the related art.

When the Raman reporter (a molecule) has a binding affinity for the metal of the metal nanocore, a self-assembled monolayer of the Raman reporter may be formed on the metal nanocore to which a bare surface of the metal is exposed.

To prepare the metal nanoparticles and design the shape of the metal nanoparticles, as known in the art, an organic surfactant capable of inhibiting growth of the metal nanoparticles or inducing the growth of the metal nanoparticles in a certain direction while providing the metal nanoparticles with a proper reducing property, and/or stabilizing the nanoparticles may be used as well-known and widely used in the art. In this case, an organic acid is used in combination with the organic surfactant, or an organic acid capable of replacing the surfactant is used. However, organic functional groups derived from the organic surfactant or the organic acid are bound to surfaces of the metal nanoparticles synthesized by such a method due to the very strong binding affinity for a metal material of the metal nanoparticles. Therefore, it may be difficult to uniformly and completely cover (replace) the surfaces of the metal nanoparticles with a desired functional group due to the functional groups strongly bound to the surfaces of the metal nanoparticles.

However, in the step a), the metal nanocore is entirely prepared from the buffer solution and the metal precursor in a state in which the organic acid or the organic surfactant is excluded. As described above, when the dispersion is stably retained in the buffer solution, the prepared metal nanocore may merely have a surface state of the metal itself. Owing to such a surface state of the metal, the Raman reporter (i.e., an organic compound having a binding affinity for the metal nanocore and includes a Raman-active molecule) is spontaneously bound to the metal nanocore in a uniform and homogeneous fashion. Even when the metal nanocore has a shape with unevenness, which is referred to as a "nano-star", the self-assembled monolayer of the Raman reporter may be stably formed.

The Raman-active molecule may include a surface-intensified Raman-active molecule, a surface-enhanced resonance Raman-active molecule, a Hyper Raman-active molecule, or a Coherent anti-Stokes Raman-active molecule. The Raman-active molecule may have Raman signals and fluorescence signals at the same time, or may have Raman signals.

As a specific example, the Raman-active molecule may be selected from the group consisting of cyanine, fluorescein, rhodamine, 7-nitrobenz-2-oxa-1,3-diazole (NBD), phthalic acid, terephthalic acid, isophthalic acid, cresyl fast violet, cresyl blue violet, brilliant cresyl blue, para-aminobenzoic acid, erythrosine, biotin, digoxigenin, phthalocyanine, azomethine, xanthine, N,N-diethyl-4-(5'-azobenzotriazolyl)-phenylamine, aminoacridine, and a combination thereof. Examples of the cyanine may include Cy3, Cy3.5, or Cy5. Examples of the fluorescein may include carboxyfluorescein (FAM), 6-carboxy-2',4,4',5',7,7'-hexachlorofluorescein (HEX), 6-carboxy-2',4,7,7'-tetrachlorofluorescein (TET), 5-carboxy-4',5'-dichloro-2',7'-dimethoxyfluorescein, 6-carboxy-4',5'-dichloro-2',7'-dimethoxyfluorescein (Joe), 5-carboxy-2',4',5',7'-tetrachlorofluorescein, 5-carboxyfluorescein, or succinyl fluorescein. Examples of the rhodamine may include tetramethylrhodamine (Tamra), 5-carboxyrhodamine, 6-carboxyrhodaminerhodamine, 6G (Rhodamine 6G: R6G), tetramethyl rhodamine isothiol (TRIT), sulforhodamine 101 acid chloride (Texas Red dye), carboxy-X-rhodamine (Rox), or rhodamine B.

As another specific example, the Raman-active molecule may be a Raman-active molecule in the form of a benzene ring, and the Raman-active molecule in the form of a benzene ring may include 4-aminothiophenol (4-ATP), 4-mercaptobenzoic acid (4-MBA), phenyl isothiocyanate (PITC), benzenethiol (BT), 1,4-benzenedithiol (BDT), biphenyl-4,4'-dithiol (BPDT), p-terphenyl-4,4''-dithiol (TPDT), 4-bromobenzenethiol (4-BBT), 4-chlorobenzenethiol (4-CBT), 3,3'-diethylthiatricarbocyanine iodide (DTTC), and the like.

Favorably, the Raman reporter may be an organic compound (i.e., an organic molecule) that has a binding affinity for each of a metal (a first metal) of the metal nanocore and a metal (a second metal) of the metal shell and includes the Raman-active molecule.

Specifically, the Raman reporter includes the Raman-active molecule, and may have a first functional group spontaneously binding to the first metal and a second functional group spontaneously binding to the second metal (a second metal of the second metal precursor).

In the step c), when the metal shell is formed, it is favorable that the second functional group may provide a nucleation site for a more smooth and uniform second metal shell, and remarkably improve the binding affinity between the second metal shell and the metal nanocore in which the Raman reporter is fixed. That is, because the Raman reporter has a binding affinity for the metal shell as well as the metal nanocore, the self-assembled monolayer may be chemically bound to the metal nanocore via the first functional group, and may also be chemically bound to the metal shell via the second functional group.

The functional group (the first or second functional group) may be suitable in consideration of the metal as long as the functional group is a functional group known to spontaneously bind to the corresponding metal. As one specific example, when the first metal and the second metal are each independently gold or silver, the functional group (the first or second functional group) may be a thiol group (—SH), a carboxyl group (—COOH), an amine group (—NH$_2$), or the like, but the present invention is not limited to the specific type of the functional group. Specific examples of the Raman reporter having both of the first functional group and the second functional group may include 1,4-benzenedithiol (BDT), biphenyl-4,4'-dithiol (BPDT), p-terphenyl-4,4''-dithiol (TPDT), and the like, but the present invention is not limited to the spherical material of the Raman reporter.

As described above, when the Raman-active molecule having a binding affinity for the metal of the metal nanocore is spontaneously bound to (fixed in) the metal nanocore via the first functional group, the self-assembled monolayer of the Raman reporter may be formed on the metal nanocore.

The formation of such a self-assembled monolayer may allow a single molecular film of the Raman reporter having a highly uniform thickness to be homogeneously formed on the entire surface of the metal nanocore although the nano-star shape of the metal nanocore is a shape having high anisotropy.

Also, the formation of the self-assembled monolayer of the Raman reporter may allow a nanogap having a highly uniform size to be formed between the metal nanocore and the metal shell, thereby forming a uniformly controlled hot spot on the entire region of the Raman-active nanoparticles.

When the nanogap (hot spot) between the metal nanocore and the metal shell is formed by the Raman reporter bound to the metal nanocore, the length (size) of the Raman reporter may be less than or equal to 3 nm, and particularly in a range of 0.5 to 2 nm in terms of the formation of the hot spot in which signals are more strongly enhanced.

The step b) of fixing the Raman reporter in the metal nanocore may include preparing a mixed solution containing the Raman reporter and the metal nanocore prepared in the step a) and stirring the mixed solution.

Specifically, the step b) may include: b1) mixing the metal nanocore prepared in the step a) and the Raman reporter so that the molar concentrations of the metal nanocore and the Raman reporter are in a range of 0.01 to 1 nM and 10 to 1,000 μM, respectively, to prepare a mixed solution; reacting the mixed solution at room temperature for 10 to 30 minutes while stirring by sonication; and b4) separating and recovering the metal nanocore in which the Raman reporter is fixed (the self-assembled monolayer of the Raman reporter is formed). In this case, the mixed solution may be an aqueous mixed solution. In this case, the mixed solution may further include a water-soluble phosphorus-based aromatic compound such as bis(p-sulfonatophenyl) phenylphosphine (BSPP), and the like in order to prevent coagulation of the metal nanocore.

After the step b) is performed, the step c) of forming the metal shell, which surrounds the nanocore in which the Raman reporter is fixed, from the second reaction solution in which the second metal precursor is mixed with the nanocore in which the Raman reporter is fixed may be performed. The nanocore (metal nanocore) in which the Raman reporter is fixed may be a metal nanocore in which the self-assembled monolayer of the Raman reporter is formed.

The metal shell formed in the step c) has an advantage in that, when a nanogap between the metal shell and the metal nanocore is formed by the Raman reporter fixed in the nanocore, the hot spot is not formed in the form of a dot or line but formed in a plane form corresponding to a surface of the metal nanocore, thereby obtaining stronger Raman scattering signals. Also, when the size of the nanogap is determined by the self-assembled monolayer of the Raman reporter, the self-assembled monolayer may be formed with the Raman reporter simply designed to have a proper size, thereby controlling the size of the nanogap over the entire region of a nano-star uniformly and precisely.

In addition to the second metal precursor and the nanocore (metal nanocore) in which the Raman reporter is fixed, the second reaction solution may further contain a surfactant capable of serving as a reducing agent for reducing the second metal precursor and serving as a stabilizing agent for stabilizing the metal nanocore and the prepared Raman-active nanoparticles, or may further contain a surfactant and an organic acid.

When the metal shell is formed using the surfactant, the metal shell may be formed in the form of a highly thin, uniform and smooth film so that the prepared Raman-active nanoparticles have a shape substantially corresponding to the shape of the metal nanocore having a nano-star shape.

It is favorable that the metal shell in the form of such a smooth film (i.e., a film having low surface roughness) may more uniformly fix a receptor that specifically binds to an analyte rather than the Raman-active nanoparticles, and may also fix a larger amount of the receptor.

The surfactant contained in the second reaction solution may be a cationic surfactant. The cationic surfactant may be a quaternary ammonium salt, and the quaternary ammonium salt is a nitrogen-containing compound that includes a compound bound to a chain-like alkyl as well as a nitrogen-containing heterocyclic compound (such as a cyclic nitrogen compound). In this case, the nitrogen-containing heterocyclic compound may include a pyridinium salt, quinolinium, imidazolium, or a mixture thereof.

Favorably, the second metal of the second metal precursor may be spontaneously reduced. In this case, the quaternary ammonium salt-based surfactant may satisfy the following Chemical Formula 1 so that the second metal is slowly reduced to form the metal shell in the form of a very smooth and compact thin film.

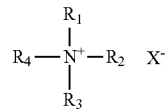

[Chemical Formula 1]

wherein $R_1$, $R_2$, and R3 may be each independently a C1-C3 alkyl group, R4 may be a C10-C19, favorably C14-C18 alkyl group, and X that is a counter ion of an ammonium ion may be a halogen. Specific examples of the quaternary ammonium salt-based surfactant satisfying Chemical Formula 1 may include hexadecyl-trimethylammonium chloride (CTAC), hexadecyl-trim-ethyl-ammonium bromide (CTAB), and the like, but the present invention is not limited to the materials of the spherical quaternary ammonium salt-based surfactant.

To form a metal shell which is thinner and has low surface roughness, the second reaction solution may further contain an organic acid in addition to the quaternary ammonium salt-based surfactant. The organic acid may include one or more selected from the group consisting of acetic acid, propionic acid, fumaric acid, malic acid, succinic acid, glycolic acid, butyric acid, palmitic acid, formic acid, lactic acid, oxalic acid, oxaloacetic acid, tartaric acid, ascorbic acid, citric acid, and isocitric acid, but the present invention is not particularly limited thereto.

The second metal of the second metal precursor may also be a metal that generates surface plasmons by means of interaction with light. In this case, the second metal may include gold, silver, platinum, palladium, nickel, aluminum, copper, or a mixture or an alloy thereof. However, aside from the first metal, the second metal may be gold or silver in consideration of biostability. In the second metal according to one favorable example, the second metal precursor may be a gold precursor such as $HAuCl_4$, $HAuBr_4$, $NaAuCl_4$, $AuCl_3 \cdot 3H_2O$, $NaAuCl_4 \cdot 2H_2O$, or a mixture thereof. Optionally, the second metal precursor may be a silver precursor such as $AgNO_3$, and the like, but the present invention is not particularly limited thereto.

More specifically, the step c) may include mixing a surfactant solution, a second metal precursor solution, and a metal nanocore dispersion in which the Raman reporter is fixed to prepare a second reaction solution, and reacting the second reaction solution at a temperature of 15 to ° C., and favorably room temperature for less than 20 minutes, and particularly 5 to 15 minutes to prepare a metal shell. Further specifically, the second reaction solution may be prepared by mixing a surfactant solution, a second metal precursor solution, a metal nanocore dispersion in which the Raman reporter is fixed, and an organic acid solution. The violent stirring may be performed during the reaction, and the termination of the reaction may be performed by separating and recovering a solid phase using centrifugation, and the like.

The molar concentration of the surfactant in the surfactant solution may be in a range of 0.1 to 0.3 M, the molar concentration of the second metal precursor in the second metal precursor solution may be in a range of 1 to 20 mM, the molar concentration of the metal nanocore in the metal nanocore dispersion in which the Raman reporter is fixed may be in a range of 0.01 to 0.5 nM, and the molar concentration of the organic acid in the organic acid solution may be in a range of 0.01 to 0.3 M, but the present invention is not particularly limited thereto.

Upon preparation of the second reaction solution, the surfactant solution and the second metal precursor solution may be mixed so that the molar ratio R2 obtained by dividing the number of moles of the surfactant by the number of moles of the second metal precursor may be in a range of 200 to 500, and particularly in a range of 300 to 500. When the second reaction solution further includes the organic acid, the organic acid solution may be mixed so that the molar ratio R3 obtained by dividing the number of moles of the surfactant by the number of moles of the organic acid may be in a range of 0.01 to 0.20, and particularly in a range of 0.05 to 0.1.

As such, the molar ratio of R2 and also the molar ratios of R2 and R3 are conditions suitable for generating a compact and smooth thin film (a metal shell) of the second metal while substantially retaining the shape of the metal nanocore having a nano-star shape because the second metal is spontaneously reduced at room temperature without any application of separate energy, and is also reduced at a proper rate.

The metal nanocore dispersion may be mixed so that the molar ratio of the second metal precursor and the metal nanocore is in a range of 1 (second metal precursor):$1 \times 10^{-7}$ to $1 \times 10^{-5}$ (metal nanocore). In this case, the second metal precursor solution and the metal nanocore dispersion are first mixed, and the surfactant solution or the surfactant solution and the organic acid solution may then be mixed so that the metal shell can be uniformly formed on the metal nanocore(s).

Specifically, the step c) may include: c1) mixing a second metal precursor solution and a metal nanocore dispersion to prepare a precursor-nanocore mixed solution; and c2) mixing a surfactant solution or a surfactant solution and an organic acid solution with the precursor-nanocore mixed solution to prepare a second reaction solution and reacting the second reaction solution at a temperature of 15 to 40° C., and favorably room temperature for less than 20 minutes to prepare Raman-active nanoparticles.

In the step c), the Raman-active nanoparticles, which include a metal nanocore, a self-assembled monolayer of the Raman reporter surrounding the metal nanocore, and a metal shell surrounding the self-assembled monolayer, may be prepared.

When the metal shell having a smooth surface, which has a very uniform and thin thickness, is formed on the entire region of the metal nanocore on which the self-assembled monolayer of the Raman reporter is formed, the prepared Raman-active nanoparticles may have protrusions stemming from the nano-star shape of the metal nanocore, and may have a shape substantially corresponding to the nano-star shape of the metal nanocore. In this case, the corresponding shape may be a shape in which protrusions protrude from a nano-star of the metal nanocore at substantially the same positions as those of the protrusions, and thus may refer to a shape in which substantially the same number of protrusions as the protrusions protrude from a nano-star of the metal nanocore.

In the step c), the Raman-active nanoparticles, which have an average size of 150 nm or less (i.e., a diameter calculated from a sphere having the same volume), particularly an average size of 100 nm or less, substantially a size of 40 to 100 nm, more substantially a size of 60 to 100 nm, and further substantially a size of 65 to 80 nm, may be prepared.

After the step c), the method of preparing Raman-active nanoparticles according to one embodiment of the present invention may further include: d) fixing a receptor, which binds (specifically binds) to an analyte, in the metal shell.

The step d) may be performed by mixing the receptor with the prepared Raman-active nanoparticle dispersion. In this case, the types of receptors may be fixed according to the protocols known in the art.

The receptor may be suitable as long as the receptor is any material known to form an enzyme-substrate, antigen-antibody, protein-protein, or DNA-DNA complementary bond with the analyte. In this case, the receptor may include a functional group (for example, a thiol group, a carboxyl group, an amine group, or the like) spontaneously binding to the second metal of the metal shell. In this case, the receptor may be spontaneously bound to the metal shell via the functional group.

The analyte may be a biogenic material (including viruses) or a non-biogenic material. The biogenic material may include a cell ingredient. Specifically, the analyte may be a biomaterial for labeling a lesion having lesion specificity, a lesion indicator, a pathogen, a drug, an organic compound, a biochemical material, or a bio-derived material. The biochemical material or the bio-derived material may include a peptide, a carbohydrate, a protein, a protein complex, a lipid, a metabolite, an antigen, an antibody, an enzyme, a substrate, an amino acid, an aptamer, a sugar, a nucleic acid, a nucleic acid fragment, a peptide nucleic acid (PNA), a cell extract, or a mixture thereof, but the present invention is not particularly limited thereto.

The prepared Raman-active particles may be used in vivo or in vitro.

The present invention includes the Raman-active nanoparticles prepared by the preparation method as described above.

Hereinafter, the Raman-active nanoparticles according to the present invention will be described in detail. In this case, for the Raman-active nanoparticles, a metal nanocore, a nano-star shape, a Raman reporter, a self-assembled monolayer, a metal shell, an analyte, a receptor, and the like are similar to and the same as previously described in the method of preparing Raman-active nanoparticles. Therefore, the Raman-active nanoparticles according to the present invention may encompass all the same contents as previously described in the method of preparing Raman-active nanoparticles.

The Raman-active nanoparticles according to the present invention include a metal nanocore having a nano-star shape; a self-assembled monolayer including a Raman reporter fixed in the metal nanocore; and a metal shell surrounding the self-assembled monolayer, and have a protruding structure due to the nano-star shape of protrusions.

The Raman-active nanoparticles according to the present invention may include a metal nanocore having a nano-star shape. The metal nanocore having a nano-star shape may have a central region having a size of 10 to 50 nm, and particularly approximately 10 to 40 nm, and protrusions protruding from the central region to taper in a protruding direction and having a size of 5 to 70 nm, particularly 5 to 50 nm, and more particularly approximately 10 to 50 nm. As one specific example, the nanocore may have 3 or more protrusions, and particularly 3 to 8 protrusions.

When the Raman-active nanoparticles include the nanocore having a nano-star shape, the Raman-active nanoparticles themselves may have a hot spot. Accordingly, the Raman-active nanoparticles have advantages in that Raman signals may be enhanced only by the Raman-active nanoparticles, there is no limitation on the size of the analyte, and the LSPR wavelength may be easily tuned by the size and spherical shape of the nano-star, and thus may be tuned to a region of 800 nm. By the LSPR wavelength spanning to a region of 800 nm, it is meant that the analyte may be subjected to Raman analysis (SERS analysis) by irradiation with near-infrared rays.

Also, the Raman-active nanoparticles according to the present invention have an advantage in that the Raman-active nanoparticles may have uniform and stable SERS activity over the entire region of the nanocore because the Raman reporter is fixed in the nanocore in the form of a self-assembled monolayer even when the nanocore has a complex shape having very high anisotropy, which is referred to as the nano-star. In this case, when the Raman reporter is positioned in the hot spot, the Raman signals may be remarkably enhanced.

In addition, the Raman-active nanoparticles according to the present invention have an advantage in that a physically/chemically vulnerable organic component (i.e., a Raman reporter) is stably protected from external environments because the self-assembled monolayer is surrounded by the metal shell so that the self-assembled monolayer is protected by the metal shell.

Additionally, the Raman-active nanoparticles according to the present invention have an advantage in that, when the Raman reporter has a first functional group spontaneously binding to the first metal (i.e., a metal nanocore) and a second functional group spontaneously binding to the second metal (i.e., a metal shell), the Raman-active nanoparticles have excellent durability and stability because the nanocore, the self-assembled monolayer, and the metal shell are very strongly bound to each another.

Further, the Raman-active nanoparticles according to the present invention may further enhance the Raman signals because the nanogap (a hot spot) having a uniform size, which corresponds to the thickness of the self-assembled monolayer (corresponding to the size of the Raman reporter), may be formed between the metal shell and the nanocore when the Raman reporter is fixed in the nanocore in the form of a self-assembled monolayer.

The metal shell bound to the self-assembled monolayer via the functional group (a second functional group) of the Raman reporter may have a thickness of 3 to 20 nm, and particularly a thickness of 5 to 15 nm. In this case, the metal shell may be a compact film having a thin and uniform thickness.

Owing to the metal shell having such a thin and uniform thickness, the Raman-active nanoparticles may have a shape corresponding to the nano-star shape of the metal nanocore. When the Raman-active nanoparticles have a shape corresponding to the nano-star shape of the metal nanocore, the enhancement of the Raman signal may be remarkably improved due to the synergistic action caused by a metal shell structure including a nano-star shape of the nanocore, a nanogap formed by the self-assembled monolayer of the Raman reporter, and a shape corresponding to that of the nano-star.

The Raman-active nanoparticles may further include a receptor fixed in the metal shell to bind to the analyte, and the receptor may include a functional group spontaneously binding to the metal shell. The receptor specifically binding to the analyte may allow the analyte to be analyzed and detected by Raman spectroscopy, and may also allow the analyte to be sensed and imaged by the Raman spectroscopy.

The aforementioned Raman-active nanoparticles may be used in vivo or in vitro.

FIG. 1 is a scanning electron microscope image for observing the metal nanocore prepared according to one embodiment of the present invention.

Specifically, the metal nanocore of FIG. 1 is prepared by mixing 500 µL of a $HAuCl_4$ solution (with a concentration of 40 mM) with 100 mL of a HEPES buffer solution (pH=7.2; having a concentration of 140 mM) (R1=700) and stirring the resulting mixture at room temperature and 1,000 rpm for 30 minutes. The prepared metal nanocore was stored at a temperature of 4° C. in a HEPES buffer solution having a concentration of 140 mM prior to observation of the metal nanocore followed by fixing the Raman reporter in the metal nanocore.

As shown in FIG. 1, it can be seen that the Au nanocore having a nano-star shape was prepared, and it can also be seen that the Au nanocore having a nano-star shape, in which the central region had a size of approximately 30 nm and the protrusions had a length of approximately 20 to 30 nm, was prepared.

FIG. 2 is an optical image for observing the Au nanocore stored in the HEPES buffer solution. As shown in FIG. 2, it can be seen that the dispersion of the Au nanocore was stably maintained without any aid of additional surfactants or organic dispersing agents.

FIG. 3 is a graph for measuring the optical absorbance of the optical absorbance of a metal nanocore prepared according to one embodiment of the present invention. In the samples of FIG. 3, $R_{[HEPES/Au]}=700$ (pH 7.2) represents an Au nanocore prepared in the same manner as in the nanocore of FIG. 1, except that the Au nanocore is prepared under the conditions in which R1 is 700 and the pH of the HEPES buffer solution is pH 7.2, $R_{[HEPES/Au]}=500$ (pH 7.2) represents an Au nanocore prepared in the same manner as in the nanocore of FIG. 1, except that the Au nanocore is prepared under the conditions in which R1 is 500 and the pH of the HEPES buffer solution is 7.2, and $R_{[HEPES/Au]}=500$ (pH 5.2) represents an Au nanocore prepared in the same manner as in the nanocore of FIG. 1, except that the Au nanocore is prepared under the conditions in which R1 is 500 and the pH of the HEPES buffer solution is 5.2.

As observed by the scanning electron microscope, it was confirmed that the lengths of the protrusions of the nano-star varied according to the R1 and the pH of the buffer solution, and the Au nanocore having a nano-star shape, which had well-developed protrusion with an increasing R1 and an increasing pH of the buffer solution, was prepared.

As shown in FIG. 3, it can be seen that, when the hot spot was formed by the protrusions protruding from the central region, the LSPR wavelength was tuned according to such a degree of development of the protrusions. Also, it can be seen that the LSPR wavelength was shifted to a longer wavelength as the protrusions were well developed. As can be seen from the $R_{[HEPES/Au]}=700$ (pH 7.2) sample, it can also be seen that the LSPR wavelength was able to be tuned to a region of near-infrared rays.

FIG. 4 is a scanning electron microscope image for observing the Raman-active nanoparticles prepared by forming a self-assembled monolayer of the Raman reporter on the Au nanocore, followed by forming an Au shell using a second reaction solution.

Specifically, the Au nanocore ($R_{[HEPES/Au]}=700$ (pH 7.2) sample) was recovered from a reaction solution by centrifugation (at 8,000 rpm for 10 minutes), mixed with 4 mL of a 1 mM bis(p-sulfonatophenyl)phenylphosphine (BSPP) dihydrate dipotassium salt solution, and sonicated for 10 minutes to prepare an Au nanocore dispersion with a molar concentration of 0.1 nM. 4 mL of the Au nanocore dispersion and 200 µL of 1,4-benzenedithiol (BDT) with a molar concentration of 10 mM were mixed, and the resulting mixture was sonicated for 10 minutes, and then centrifuged at 6,000 rpm for 10 minutes to recover the Au nanocore on which the self-assembled monolayer of BDT serving as the Raman reporter was formed. The recovered Au nanocore on which the self-assembled monolayer was formed was dispersed in 4 mL of deionized water (with a molar concentration of 0.1 nM), mixed with 100 μL of 10 mM $HAuCl_4$ in the dispersion, and further mixed with 2 mL of a 0.2M CTAC solution and 0.2 mL of a 0.2M ascorbic acid solution to prepare a second reaction solution. Thereafter, the second reaction solution was reacted for 10 minutes while stirring, and then centrifuged (at 5,000 rpm for 10 minutes) to prepare the Raman-active nanoparticles (Raman-active nanoparticles shown in FIG. 4).

As shown in FIG. 4, it can be seen that the prepared Raman-active nanoparticles had a shape corresponding to the nano-star shape of the metal nanocore, and also that the metal shell stably surrounded the entire region of the metal nanocore in which the Raman reporter was fixed in the form of smooth and compact rods having a uniform thickness.

FIG. 5 is a graph showing the surface-enhanced Raman scattering (SERS) spectrum of the prepared Raman-active nanoparticles (a sample of FIG. 4). The SERS spectrum was obtained by irradiating the Raman-active nanoparticles with light of 514 nm, 633 nm, or 785 nm using a Micro Raman system (Horiba).

As shown in FIG. 5, it can be seen that the surprisingly strong Raman scattering signals were obtained by light having a near-infrared band of 785 nm, and also that the strong Raman signals observed in the vicinity of a 1,100 $cm^{-1}$ region and 1,550 $cm^{-1}$ region were coincident with the innate SERS signals of the Raman reporter (DBT).

Although the subject matters of the present invention have been described in the present invention with reference to certain subject matters and limited examples thereof and the accompanying drawings, it should be understood that the subject matters and limited examples described herein are provided to aid in understanding the present invention more comprehensively, but are not intended to limit the present invention. Therefore, it will be apparent to those skilled in the art to which the present invention belongs that various modifications can be made from the detailed description of the present invention.

Thus, the scope of the present invention is not intended to be limited to the examples described herein, and thus all types of the appended claims, and equivalents or equivalent modifications thereof come within the scope of the present invention.

The invention claimed is:

1. A method of preparing Raman-active nanoparticles, the method comprising:
  a) preparing a gold nanocore having a nano-star shape from a first reaction solution in which a first gold precursor is mixed with only a 4-(2-hydroxyethyl)-1-piperazineethanesulfonic acid (HEPES) buffer solution;
  b) fixing a 1,4-benzenedithiol (BDT) to the gold nanocore after a) is performed; and
  c) forming a gold metal shell, which surrounds the nanocore in which the BDT is fixed, from a second reaction solution in which a second gold precursor is mixed with the nanocore in which the BDT is fixed after b) is performed,
  wherein a size and/or shape of the nanocore is adjusted by controlling a factor of a molar ratio of the HEPES of the buffer solution to the first gold precursor in a) to be about 700 and controlling the pH to be about 7.2, such that the resulting Raman-active nanoparticles elicit Raman signals coincident with innate surface-enhanced Raman scattering (SERS) signals of the BDT,
  wherein the BDT has a binding affinity for each of the gold nanocore and the gold metal shell.

2. The method of claim 1, wherein a self-assembled monolayer of the BDT surrounding the metal nanocore is formed in the fixing of the Raman reporter in the metal nanocore.

3. The method of claim 1, wherein the factor further comprises a pH of the buffer solution.

4. The method of claim 1, wherein the second reaction solution comprises a surfactant, or comprises a surfactant and an organic acid.

5. The method of claim 1, further comprising, after the forming of the metal shell from the second reaction solution:
  d) fixing a receptor, which binds to an analyte, in the metal shell.

\* \* \* \* \*